United States Patent
Sanpei et al.

(10) Patent No.: US 6,590,126 B1
(45) Date of Patent: Jul. 8, 2003

(54) INDUSTRIAL PROCESS FOR THE PRODUCTION OF DIPHENYL SULFONE COMPOUNDS

(75) Inventors: Syuichiro Sanpei, Koriyama (JP); Masayuki Hanzawa, Koriyama (JP); Yasuyuki Suzuki, Koriyama (JP); Minoru Kaeriyama, Odawara (JP); Tomoya Hidaka, Ichihara (JP); Toru Kawabe, Nakago-mura (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/937,248

(22) PCT Filed: Mar. 17, 2000

(86) PCT No.: PCT/JP00/01639

§ 371 (c)(1),
(2), (4) Date: Sep. 21, 2001

(87) PCT Pub. No.: WO00/56705

PCT Pub. Date: Sep. 28, 2000

(30) Foreign Application Priority Data

Mar. 23, 1999 (JP) .......................................... 11-078625

(51) Int. Cl.[7] ............................................. C07C 315/04
(52) U.S. Cl. ............................................. 568/33; 568/34
(58) Field of Search .......................... 568/28, 27, 34, 568/33, 32; 570/258

(56) References Cited

U.S. PATENT DOCUMENTS 3,784,518 A * 1/1974 Paulik 5,284,978 A   2/1994 Kinishi et al.

FOREIGN PATENT DOCUMENTS

JP   58-164131   4/1985
JP   04-000715   7/1993

OTHER PUBLICATIONS

CA:122:238840 abs of Tetrahedron Lett by Joseph et al 36(4) pp 609–12 1995.*

CA:120:120832 abs of JP05255234 Oct. 1993.*

CA: 129:4497 abs of JP10114735 May 1998.*

* cited by examiner

Primary Examiner—Jean F. Vollano
(74) Attorney, Agent, or Firm—Dennis G. LaPointe; Mason Law, P.A.

(57) ABSTRACT

A process for producing compounds of general formula (II) useful as the developer for leuco dyes to be used in thermosensible papers, which is excellent in productivity, economical efficiency and safety and permits the production of the compounds from constantly available raw materials. This process is improved in productivity, economical efficiency and safety as compared with those of the prior art both by shortening the production time by the use of, e.g., an alkyl iodide, RI, which is more reactive than alkyl bromides which have been used in the prior art, and by attaining the complete recovery and reuse of iodine by incorporating into the process the iodine recovery step of recovering iodine from the manufacturing wastewater and reacting this iodine with an alcohol to thereby self-produce an alkyl iodide.

10 Claims, No Drawings

INDUSTRIAL PROCESS FOR THE PRODUCTION OF DIPHENYL SULFONE COMPOUNDS

This application is a 371 of PCT/JP00/01639 filed Mar. 17, 2000, now WO 00/56705.

The present invention relates to industrial processes for the production of diphenyl sulfone compounds represented by Formula (II) and useful as developers for leuco dyes to be used in thermal recording papers, and in more detail, to processes for the efficient production of the said diphenyl sulfone compounds by the recovery and reuse of harmful halogen compounds without discharging them into the environment.

BACKGROUND ART

Processes for the preparation of diphenyl sulfone compounds of Formula (II) are disclosed in Japanese Patents Laid-open Nos. Sho 58-20493, Sho 58-82788, Sho 60-13852 and Sho 60-56949, that 4,4'-dihydroxydiophenyl sulfone is reacted with a halogen compound, such as alkyl halide, in a polar solvent, such as dimethylformamide or alcohol, in the presence of an alkali. These processes have a drawback of difficulty to improve the selectivity of reactions because of the use of solvents that dissolve reaction reagents and products well. There was a problem that noticeable amounts of diether derivatives, i.e., 4,4'-disubstituted hydroxydiphenyl sulfones, are produced as byproducts.

WO 91/11433 has reported that a reaction of a mole of 4,4'-dihydroxydiphenyl sulfone with an alkyl halide in the presence of 1.5 to 3 moles of alkali in 0.3 to 1.5 parts by weight of an aqueous solvent to a part by weight of 4,4'-dihydroxydiphenyl sulfone results in satisfactory selectivity and yield. However, when alkyl chlorides are used, it takes a long time to complete the reaction because of their low reactivity. Besides, alkyl iodides are expensive. Therefore, alkyl halides able to use in industry are practically limited to alkyl bromides. The said WO patent reports only examples of using alkyl bromides.

If an alkylation is carried out using an alkyl bromide under the above reaction conditions, crystals are deposited as the reaction proceeds. The inside of the system becomes viscous and heterogeneous, resulting in insufficient stirring. Therefore, there is a problem of incompletion of the reaction.

Of compounds of Formula (II) useful as developers for leuco dyes to be used in thermal recording papers, compounds where R is isopropyl are produced using isopropyl bromide, which is hardly produced domestically. Therefore it is difficult to procure the starting material stably.

It is an object of the present invention to provide industrial processes for the production of diphenyl sulfone compounds of Formula (II) by using alkylating agents that are supplied stably, instead of alkyl bromide, with productivity, economical efficiency and safety.

DISCLOSURE OF THE INVENTION

The inventors of the present invention studied various alkylations, such as those with alkyl sulfates, by addition of unsaturated hydrocarbons, and of using alkyl chlorides or alkyl iodides. As a result, it was found that use of alkyl iodides and the like could greatly shorten production times, and that almost all of alkyl iodides and the like used in the reactions could be recovered as inorganic iodide salts. An iodine recovery step in which iodine is recovered from manufacturing waste water containing the salts and reacted with an alcohol to self-produce an alkyl iodide or the like, is incorporated in the production process. Then, iodine is completely recovered for reuse. The process is more improved in productivity and economic efficiency than those of the prior art. Thus, the present invention has been completed.

The present invention relates to (1) an industrial process for the production of diphenyl sulfone compounds of Formula (II)

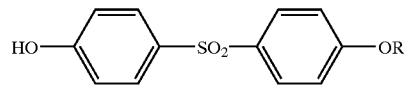

(wherein, R is straight or branched chain alkyl, straight or branched chain alkenyl, straight or branched chain alkynyl, or optionally substituted cycloalkyl), characterized in that 4,4'-dihydroxydiphenyl sulfone is reacted with a compound represented by Formula (I)

RI (wherein, R is as defined above) in the presence of a base at reaction temperature of 70 to 110° C., preferably 70 to 90° C.

It relates to (2) an industrial process for the production of diphenyl sulfone compounds according to (1), in which 0.8 to 2 moles of a compound of Formula (I) and 2 to 4 moles of a base are used to a mole of 4,4'-dihydroxydiphenyl sulfone, and the concentration of the base is made 20 to 50% by weight with water used as a solvent.

It relates to (3) an industrial process for the production of diphenyl sulfone compounds according to (1) or (2), in which a reaction time is 4 to 15 hours.

It relates to (4) an industrial process for the production of diphenyl sulfone compounds according to one of (1) to (3), in which a compound of Formula (I) is where R is isopropyl.

It relates to (5) an industrial process for the production of diphenyl sulfone compounds represented by Formula (II)

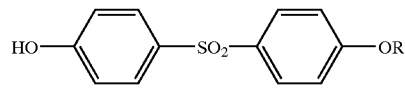

(wherein, R is as defined above), characterized by containing an iodine recovery step that 4,4'-dihydroxydiphenyl sulfone is reacted with a compound of Formula (I)

RI (wherein, R is as defined above) in the presence of a base, iodine is recovered from iodides contained in waste water, and the recovered iodine is reacted with an alcohol corresponding to a compound of Formula (I) to be used for the reaction, to give a compound of Formula (I).

It relates to (6) a process for the production of diphenyl sulfone compounds according to (5), in which a step is further incorporated that iodine is recovered from waste water discharged when a compound of Formula (I) is produced by a reaction of the previously recovered iodine with an alcohol corresponding to the compound of Formula (I) to be used for the reaction, and reused for the production of compounds of Formula (I).

It relates to (7) an industrial process for the production of diphenyl sulfone compounds according to (5) or (6), in which 4,4'-dihydroxydiphenyl sulfone is reacted with a compound of Formula (I) in the presence of a base at 70 to 110° C., preferably 70 to 90° C.

It relates to (8) an industrial process for the production of diphenyl sulfone compounds according to one of (5) to (7), in which 0.8 to 2 moles of a compound of Formula (I) and 2 to 4 moles of a base are used to a mole of 4,4'-dihydroxydiphenyl sulfone, and the concentration of the base is made 20 to 50% by weight with water used as a solvent.

It relates to (9) an industrial process for the production of diphenyl sulfone compounds according to one of (5) to (8), in which a reaction time is 4 to 15 hours.

It relates to (10) an industrial process for the production of diphenyl sulfone compounds according to one of (5) to (9), in which a compound of Formula (I) is where R is isopropyl.

Examples of compounds of Formula (I) used in the methods of the present invention include alkyl iodides such as methyl iodide, ethyl iodide, n-propyl iodide, isopropyl iodide, n-butyl iodide, isobutyl iodide, sec-butyl iodide, pentyl iodide, hexyl iodide, heptyl iodide and octyl iodide; alkenyl iodides such as allyl iodide; and cycloalkyl iodides such as cyclohexyl iodide.

In the present invention, compounds of Formula (I) (hereinafter abbreviated as alkyl iodides and the like) are preferably used 0.8 to 2 equivalents, more preferably 1.0 to 1.6 equivalents, to 4,4'-dihydroxydiphenyl sulfone.

Generally, alkyl iodides and the like are more reactive than alkyl bromides and the like, so that selectivity is not good. For example, production rates of monoalkyl and dialkyl products of 4,4'-diphenyl sulfone are reduced. The inventors of the present invention, however, found out that, if water is used as a reaction solvent, selectivity is not deteriorated, because solubility of alkyl iodides and the like to water is lower than that of alkyl bromides and the like (for example, solubility of isopropyl bromide: 0.381 g/100 g of water; and isopropyl iodide: 0.139 g/100 g of water).

As describe above, solubility of alkyl bromides and the like to water is larger than that of alkyl iodides and the like. Thus, there is a problem that alkyl bromides and the like are susceptible to hydrolysis by bases that are not forming salts with 4,4'-dihydroxydiphenyl sulfone. Therefore, it is necessary to use considerably excessive amounts of alkyl bromides and the like and bases in order to increase reaction conversion rates. In the case of alkyl iodides and the like, which are less soluble in water and more reactive, reaction conversion rates can be improved to 95% from 70% of the prior art, by using only 1.5 equivalents.

The present invention is characterized by a reaction using an alky iodide or the like in the presence of a base in a reaction temperature range between 70 and 110° C., preferably 70 and 90° C.

Alkyl iodides and the like are more reactive and have higher boiling points than alkyl bromides and the like, so that reaction temperatures can be raised at ordinary pressure without using special apparatuses. Therefore, reaction efficiency is improved and reactions are completed in shorter times than when alkyl bromides and the like are used. For example, the reaction is completed in about 8 hours when it is carried out using 1.07 equivalents of isopropyl iodide to 4,4'-dihydroxydiphenyl sulfone at 70° C. However, the same reaction but using isopropyl bromide does not finish completely in even twice a longer time of 16 hours. An alkylation using isopropyl iodide at a reaction temperature of 90° C. finishes in about 4 hours. Compared to it, it is impossible to carry out a reaction with isopropyl bromide at a reaction temperature of 90° C. except using a special apparatus. Reactions using isopropyl iodide can be carried out at temperatures above the boiling points of alkyl iodides and the like, if special apparatuses are used for reactions under pressure and other cases. Reaction efficiency is improved in terms of the shortening of reaction times and the like. This is however not preferable for industrial use.

Examples of bases used as acid removing agents include alkali metal hydroxides such as sodium hydroxide and potassium hydroxide; alkaline earth metal hydroxides such as magnesium hydroxide and calcium hydroxide; or alkali metal carbonates such as sodium carbonate and potassium carbonate. Alkali metal hydroxides are particularly preferred.

An amount of a base used gives great influence on reaction selectivity, together with an amount of water used as a reaction solvent: It is favorable to use 2 to 4 moles, preferably 2.2 to 3.2 moles, of a base to a mole of 4,4'-dihydroxydiphenyl sulfone, and an amount of water to make a base concentration 20 to 50% by weight, preferably 30 to 35% by weight in order to improve reaction selectivity. Di-alkali salts of 4,4'-dihydroxydiphenyl sulfones are highly soluble in water, but mono-alkali salts of 4,4'-dihydroxydiphenyl sulfones are less soluble in water. Therefore, as reactions proceed, mono-substituted metal salts of products are deposited so that the mono-substituted products are obtained selectively. Because of this, it is favorable to use 2 equivalents or more of a base to 4,4'-dihydroxydiphenyl sulfone at the beginning of the reaction, and, when hot, an amount of water to make a base concentration 20% by weight or more and to dissolve di-alkali salts only. If the alkali concentration is less than 20% by weight, selectivity is lowered because the mono-alkali salts of products are dissolved. On the other hand, the viscosity of the reaction solution rises in the case of 50% by weight or more, with a problem of facilities.

According to the methods of the present invention, iodine of alkyl iodides and the like used is almost all recovered as salts after the reaction. It becomes possible to recover iodine from waste water containing the salts.

The iodine recovery step consists of recovery of iodine from iodides contained in waste water discharged when a diphenyl sulfone compound of Formula (II) is produced, and production of an alkyl iodide or the like by a reaction of the recovered iodine with an alcohol corresponding to an alkyl iodide or the like to use for the reaction. Furthermore, it is favorable to contain a step of further recovering iodine from waste water when the alkyl iodide or the like is produced and reusing it for the production of an alkyl iodide.

Examples of steps of recovering iodine are described in the following: First, 4,4'-dihydroxydiphenyl sulfone is alkylated with an alkyl iodide in the presence of a base; a small amount of di-alkyl byproducts produced is separated by filtration after the completion of the reaction; the filtrate is adjusted pH with an acid; an organic solvent that dissolves the target compound, such as toluene, is added; and the resulting solution is separated to an organic layer containing the target compound and an aqueous layer containing a sodium salt of unreacted 4,4'-dihydroxydiphenyl sulfone and iodides of the base.

Then, the pH of the aqueous layer is adjusted to recover unreacted 4,4'-dihydroxydiphenyl sulfone. There are no particular restrictions on a range of pH adjustment, if on the acidic side. It is however preferable to be in the range between pH 0.5 and 4.0, particularly pH 2.0 and 3.0, in consideration of the following iodine recovery step. There are no particular restrictions on acids used. Preferred include mineral acids such as hydrochloric acid and sulfuric acid.

After most organic components are removed as described above, iodine is liberated from the aqueous layer. Examples of methods of liberation include oxidation with oxidizing agents and direct electrolysis. The oxidation with oxidizing agents is preferred from the viewpoint of equipment and cost.

Examples of oxidizing agents used include chlorine, hypochlorous acid or its salt, hydrogen peroxide, or oxygen. Chlorine is particularly preferred when taking into consideration treatments of waste water and cost. A desirable amount of an oxidizing agent used is 1 to 1.5 times, preferably 1.0 to 1.3 times, that of iodine in molar ratio. It is desirable, prior to addition of the oxidizing agent, to add an acid, such as hydrochloric acid or sulfuric acid, to adjust the solution to pH 0.5 to 3.0, preferably 1.0 to 2.0.

Methods known in the art to collect iodine from the water containing the liberated iodine include those using blow-out, ion exchange resins, copper, activated carbon or pressure melting. Any of them can be applied. The pressure melting method is preferred by taking into consideration the fact that in the reactions, most organic compounds and impurities are removed at the intermediate step and that iodine of high quality is obtained using relatively simple equipment.

In more detail, for example, the liberated iodine is separated from water by a cyclone-type centrifugal separator, then heated to 130 to 150° C. under pressure for melting, and cooled to solidify for making flakes, sublimed crystals or blocks, or powder or granules. To obtain spherical iodine, which is less sublime and easily handled, it is preferable to flow out the melt from a fine jetting nozzle in diameter at a constant speed, and to cool it to solidify by cooling gas in the midway of falling.

Known methods of preparing alkyl iodides and the like with iodine include a method of using hydrogen, iodine and methanol as starting materials in the presence of a rhodium, iridium or ruthenium catalyst; a reaction of a metal of Ia, IIa, IIIa, Ib, IIb or IVb Group in Periodic Table, iodine and an alcohol or the like at 15 to 150° C. and 1 to 50 atm; and a method of using an alcohol, iodine and red phosphorus. It is preferable to use the method of using red phosphorus when taking into consideration reaction equipment and cost.

In more detail, for example, an alkyl iodide can be synthesized by that red phosphorus is suspended in an alcohol, iodine is dropped while heating, and the product is distilled from the reaction solution. In an industrial scale, an alkyl iodide may be prepared in a way that red phosphorus suspended in an alcohol is dropped into an alcohol solution of iodine. Either anhydrous red phosphorus or red phosphorus containing water can be used. The latter is preferred because of safety. Red phosphorus containing 10 to 40 mol %, preferably 10 to 30 mol %, of water to phosphorus is used.

A reaction solvent is usually an alcohol that becomes a reaction substrate. It is possible to mix with water. It is preferable to carry out the reaction in the coexistence of water, particularly for the purpose of preventing the reaction from becoming out of control. An amount of water used is in the range of 5 to 20 ml/atom mol, preferably 10 to 15 ml/atom mol, based on an amount of iodine used. If it is less than 5 ml/atom mol, there is no effect. If more than 20 ml/atom mol is used, the reaction is checked. There are no particular restrictions on amounts of water used to suspend red phosphorus, if red phosphorus is sufficiently suspended in water within the range of giving no impediment of dropping. Water of roughly equal weight to that of red phosphorus is usually sufficient.

In this reaction, iodine ($I_2$), phosphorus and an alcohol react at a molar ratio of 3:2:6. It is however preferable to use 1 to 1.5 moles of alcohol and 0.2 to 0.3 moles of red phosphorus, to 1 atom mol of iodine, when taking into consideration reaction efficiency and iodine that is present in waste water and is used again in the recovery step.

The reaction is carried out by a method of adding iodine to an alcohol and red phosphorus, or adding phosphorus to an alcohol and iodine, at temperature of about the boiling point of the alcohol. The reaction exothermally proceeds simultaneously with the addition. Therefore, it becomes difficult to control the reaction if an addition rate is too fast. It is necessary to keep an appropriate reaction rate.

The target alkyl iodide or the like can be isolated from the reaction solution by distillation after the completion of the reaction. It can also be isolated by steam distillation. Particularly when iodine is further recovered from the residue in the vessel after the distillation, it is advantageous if contained phosphorus-iodine compounds and the like are sufficiently hydrolyzed. Steam distillation is preferred when the recovery step is taken into account.

4,4'-Dihydroxydiphenyl sulfone to be recovered in a post-treatment step, the alcohol produced from the reaction and recovered, and the re-produced alkyl iodide or the like are used again as part or the whole of starting materials for the reaction. They can be reused with no problems of reaction yields and the quality of products. Products with nearly equal quality can be prepared when compounds of Formula (II) are synthesized with alkyl bromides, or with alkyl iodides and the like and a recovery step included. The latter is more advantageous in terms of cost and productivity. It has become possible to use alkyl iodides and the like as alternative materials to alkyl bromides and the like.

BEST FORMS TO IMPLEMENT THE INVENTION

The present invention is described in more detail in reference to Examples, but is not limited to the examples.

EXAMPLE 1

26.0 g (0.624 mol) of NaOH of 96% purity and 49.4 g of water were placed in a 1000-ml four-neck flask, and dissolved at an ordinary temperature. Into the resulting solution was added 60 g (0.24 mol) of 4,4'-dihydroxydiphenyl sulfone (hereinafter abbreviated as BPS) and dissolved with stirring at 100° C. for 30 minutes. The internal temperature was cooled to 70° C. 43.7 g (0.258 mol) of isopropyl iodide was dropped over an hour and the reaction was carried out for 10 hours at the internal temperature of 70° C. A part of the reaction solution was taken out 8 hours after the reaction started, and quantitatively analyzed by HPLC to find that 4-isopropoxy-4'-hydroxydiphenyl sulfone was produced in yield of 72%.

After the reaction was completed, the reaction solution was diluted with 100 g of warm water of 50° C., and then cooled to ordinary temperature. 600 ml of methanol was added to completely dissolve the reaction products. The diluted reaction solution was quantitatively analyzed by HPLC. The results showed that a production rate of the target compound, 4-isopropoxy-4'-hydroxydiphenyl sulfone, was 75.1% (based on the amount of BPS), and that of 4,4'-diisopropoxydiphenyl sulfone, a byproduct, was 2.2% (based on the amount of BPS). A remaining rate of BPS, a starting material, was 22.7%.

EXAMPLE 2

The same amounts of NaOH, water and BPS as those in Example 1 were placed in a flask, but 61.2 g (0.36 mol) of isopropyl iodide was added. The reaction was carried out at 70° C. for 20 hours. A part of the reaction solution was taken out 8 hours and 14 hours after the reaction started, and quantitatively analyzed by HPLC. The results showed that 4-isopropoxy-4'-hydroxydiphenyl sulfone was produced in yields of 73% and 85%, respectively.

After the reaction was completed, the reaction solution was treated in the same way as that in Example 1. The diluted reaction solution was quantitatively analyzed by HPLC. The results showed that a production rate of the target compound, 4-isopropoxy-4'-hydroxydiphenyl sulfone, was 89.8% (based on the amount of BPS), and that of di-substituted byproduct was 4.8% (based on the amount of BPS). A remaining rate of BPS, a starting material, was 5.4%.

EXAMPLE 3

The same amounts of NaOH, water, BPS and isopropyl iodide as those in Example 1 were placed in a flask, but the reaction was carried out at 90° C. for 4 hours. A part of the reaction solution was taken out 3 hours after the reaction started and quantitatively analyzed by HPLC. 4-Isopropoxy-4'-hydroxydiphenyl sulfone was produced in yield of 80%.

After the reaction was completed, the reaction solution was treated in the same way as that in Example 1. The diluted reaction solution was quantitatively analyzed by HPLC. The results showed that a production rate of the target compound, 4-isopropoxy-4'-hydroxydiphenyl sulfone, was 82.0% (based on the amount of BPS), and that of di-substituted byproduct was 5.0% (based on the amount of BPS). A remaining rate of BPS, a starting material, was 13.0%.

EXAMPLE 4

26.0 g (0.624 mol) of NaOH of 96% purity and 49.4 g of water were placed in a 1000-ml 4-neck flask from whose bottom liquid can be taken out, and dissolved at an ordinary temperature. To the resulting solution was added 60 g (0.24 mol) of BPS, and stirred to dissolve at 100° C. for 30 minutes. The internal temperature was cooled to 70° C. 43.7 g (0.258 mol) of isopropyl iodide was dropped over an hour, and reacted at the internal temperature of 70° C. for 10 hours.

After the reaction was completed, the reaction solution was diluted with 110 g of warm water of 70° C., and 350 ml of toluene was added. The resulting solution was adjusted to pH 8.0 to 9.0 with dilute sulfuric acid. The aqueous layer was separated and named as Aqueous Layer 1. Further, 100 g of warm water of 70° C. was added to the remaining reaction solution and adjusted to pH 8.0 to 9.0 with dilute sulfuric acid. The aqueous layer was separated and named as Aqueous Layer 2. The toluene layer was washed with 100 g of warm water of 70° C., separated, and cooled to deposit crystals.

The crystals were filtrated, washed with toluene, and dried to give 49 g of the target compound, 4-isopropoxy-4'-hydroxydiphenyl sulfone. Its purity was 99.2% (relative area ratio in HPLC), and yield was 70% (based on the amount of BPS).

About 300 g of combined Aqueous Layers 1 and 2 was adjusted to pH 3 with dilute sulfuric acid. The deposited unreacted BPS was filtrated and washed with water for recovery. 15.3 g was recovered. A recovery rate was 25.5% (based on the amount of BPS).

An amount of iodine in the filtrate was measured by titration. The filtrate contained 99% of iodine used for the reaction.

The filtrate was adjusted to pH 1 with dilute hydrochloric acid. 22 g (0.31 mol) of chlorine gas was blown in to liberate iodine. The reaction solution was separated to iodine and an aqueous layer by a cyclone-type centrifugal separator. Titration showed that the separated aqueous layer contained iodine at a ratio of 1000 ppm to 1300 ppm. Nitrogen gas was further blown in, and cooled to recover more iodine, until an amount of iodine in the aqueous layer is below the limit of detection. The separated iodine was heated to melt in a melting vessel at 130° C. under pressure, and cooled to give 31 g of highly pure iodine. The recovery rate was 97%.

EXAMPLE 5

1209 g (20.0 mmol) of isopropanol and 58 ml of water were added to 2438 g (19.2 atom mol) of iodine, and heated to the internal temperature of 90° C. To the resulting solution was dropped, over about 2 hours, 160.9 g of red phosphorus containing water (141 g of red phosphorus and 19.8 g of water, 4.6 mol) and suspended in 153.6 ml of water while keeping the internal temperature at 90° C., and then heated at reflux for 2 hours. Steam distillation was carried out for 3 hours by passing steam through the system. The obtained fraction was washed with 600 ml of water to give 2886 g of isopropyl iodide of 98% purity (yield: 87%). Titration showed that the residue in the vessel after the steam distillation contained 11% of iodine used. The recovery rate of iodine together with isopropyl iodide was 98%.

INDUSTRIAL APPLICABILITY

When compounds of Formula (II) are synthesized, reaction times are greatly reduced if alkyl iodides and the like, instead of alkyl bromides and the like, are used as alkylating agents or the like. Besides, material conversion rates can be improved without deteriorating reaction selectivity. Iodine of alkyl iodides and the like used can be recovered as salts. Products equal in terms of cost to those produced using alkyl bromides and the like can be provided if an iodine recovery step is incorporated into the reaction process. Therefore, it becomes possible to use alkyl iodides and the like, which are stably supplied, for industrial productions. Iodine used can be recovered nearly completely. Thus, processes for efficient productions have been found without discharging harmful iodides into the environment.

What is claimed:

1. An industrial process for the production of 4-isopropoxy-4'-hydroxydiphenyl sulfone, in which an iodine recovery step is incorporated in that 4,4'-dihydroxydiphenyl sulfone is reacted with isopropyl iodide in the presence of a base, iodine is recovered from iodides contained in waste water, which comes from a reaction solvent and/or water added in a purification step, and the recovered iodine is reacted with isopropyl alcohol, to give isopropyl iodide.

2. The industrial process for the production of 4-isopropoxy-4'-hydroxydiphenyl sulfone according to claim 1, in which a step is incorporated in that iodine is further recovered from waste water, which comes from a reaction solvent and/or water added in a purification step, discharged when isopropyl iodide is produced from a reaction of the recovered iodine with isopropyl alcohol, and reused for the production of isopropyl iodide.

3. The industrial process for the production of 4-isopropoxy-4'-hydroxydiphenyl sulfone according to claim 1, in which 4,4'-dihydroxydiphenyl sulfone is reacted with isopropyl iodide in the presence of a base with water used as a solvent at 70 to 110° C.

4. The industrial process for the production of 4-isopropoxy-4'-bydroxydiphenyl sulfone according to claim 2, in which 4,4'-dihydroxydiphenyl sulfone is reacted with isopropyl iodide in the presence of a base with water used as a solvent at 70 to 110° C.

5. The industrial process for the production of 4-isopropoxy4'-hydroxydiphenyl sulfone according to claim 1, in which the reaction is carried out at a reaction temperature of 70 to 90° C.

6. The industrial process for the production of 4isopropoxy-4'-hydroxydiphenyl sulfone according to claim 2, in which the reaction is carried out at a reaction temperature of 70 to 90° C.

7. The industrial process for the production of 4-isopropoxy-4'-hydroxydiphenyl sulfone according to claim 1, in which 0.8 to 2 moles of isopropyl iodide and 2 to 4 moles of a base are used to a mole of 4,4'-dihydroxydiphenyl sulfone, and the concentration of the base is made 20 to 50% by weight with water used as a solvent.

8. The industrial process for the production of 4-isopropoxy-4'-hydroxydiphenyl sulfone according to claim 2, in which 0.8 to 2 moles of a compound of isopropyl iodide and 2 to 4 moles of a base are used to a mole of 4,4'-dihydroxydiphenyl sulfone, and the concentration of the base is made 20 to 50% by weight with water used as a solvent.

9. The industrial process for the production of 4-isopropoxy-4'-hydroxydiphenyl sulfone according to claim 1, in which a reaction time is 4 to 15 hours.

10. The industrial process for the production of 4-isopropoxy-4'-hydroxydiphenyl sulfone according to claim 2, in which a reaction time is 4 to 15 hours.

* * * * *

UNITED STATES PATENT AND TRADEMARK OFFICE
CERTIFICATE OF CORRECTION

PATENT NO. : 6,590,126 B1
DATED : July 8, 2003
INVENTOR(S) : Sanpei et al.

It is certified that error appears in the above-identified patent and that said Letters Patent is hereby corrected as shown below:

<u>Title page,</u>
Item [75], delete the city for the below inventors, and insert the following city:
"Sanpei," the correct city is -- Fukushima --;
"Hanzawa," the correct city is -- Fukushima --;
"Suzuki," the correct city is -- Fukushima --;
"Kaeriyama," the correct city is -- Kanagawa --;
"Hidaka," the correct city is -- Chiba --; and
"Kawabe," the correct city is -- Niigata --.

Item [57], ABSTRACT, insert the following formula at the end of the Abstract:

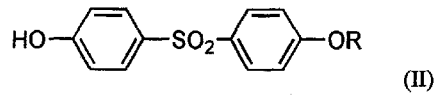
(II)

Signed and Sealed this

Thirtieth Day of September, 2003

JAMES E. ROGAN
*Director of the United States Patent and Trademark Office*